US006849257B2

(12) United States Patent
Grabowski et al.

(10) Patent No.: US 6,849,257 B2
(45) Date of Patent: Feb. 1, 2005

(54) LIPID HYDROLYSIS THERAPY FOR ATHEROSCLEROSIS AND RELATED DISEASES

(75) Inventors: Gregory Grabowski, Cincinnati, OH (US); Hong Du, Cincinnati, OH (US)

(73) Assignee: Children's Hospital Research Foundation, Cincinnati, OH (US)

(*) Notice: Subject to any disclaimer, the term of this patent is extended or adjusted under 35 U.S.C. 154(b) by 209 days.

(21) Appl. No.: 09/775,517

(22) Filed: Feb. 2, 2001

(65) Prior Publication Data

US 2003/0059420 A1 Mar. 27, 2003

Related U.S. Application Data

(60) Provisional application No. 60/180,362, filed on Feb. 4, 2000.

(51) Int. Cl.$^7$ .......................... A61K 38/46; C12N 9/18
(52) U.S. Cl. ...................................... 424/94.6; 435/197
(58) Field of Search .......................... 424/94.6; 435/197

(56) References Cited

FOREIGN PATENT DOCUMENTS

WO    WO 0156596 A1 * 8/2001

OTHER PUBLICATIONS

Bond et al., "Antiatherogenic Properties of Calcium Antagonists" (1991) J. Cardiovasc. Pharmacol., 17(Suppl. 4), S87–S93, in DRUGU, AN 1991–33729.*
Chan et al., "Prostaglandins, Prostacyclin, and Thromboxane in Cardiovascular Diseases" (1986) Drug Development Research, 7(4), 341–359, in EMBASE, AN 86158857.*
Walters et al., "Calcium Channel Blockers and Coronary Atherosclerosis: From the Rabbit to the Real World" (1994) American Heart Journal, 128(6), II SUPPL., 1309–1316, in EMBASE, AN 94379101.*
Pomerantz et al., "Biochemical Mechanisms Associated with the Lipolytic Effects of Calcium Channel Blockers" (1993) Medical Science Symposia Series (1993), 2(Drugs Affecting Lipid Metabolism), 251–260, in CAPLUS, AN 1994:498900.*
Yatsu et al., "Wolman Disease" (1997) Molecular and Genetic Basis of Neurological Disease (2nd Edition), 371–378, Editor(s): Rosenberg, Roger N. Publisher: Butterworth–Heinemann, Boston, Mass, in CAPLUS, AN 1997:338577.*
Bhakdi et al., "On the Pathogenesis of Atherosclerosis: Enzymic Transformation of Human Low Density Lipoprotein to an Atherogenic Moiety" (1995) Journal of Experimental Medicine, 182(6), 1959–71, in CAPLUS, AN 1995:978593.*
Escary et al., "Hormone–Sensitive Lipase Overexpression Increases Cholesteryl Ester Hydrolysis in Macrophage Foam Cells" (1998) Arteriosclerosis, Thrombosis, and Vascular Biology, 18(6), 991–998.*
Moran et al., "Pathologic Gene Expression in Gaucher Diseasee: Up–Regulation of Cysteine Proteinases Including Osteoclastic Cathepsin K" (Sep. 1, 2000) Blood, 96(5), 1969–1978.*
Tietge et al., "Phenotypic Correction of Lipid Storage and Growth Arrest in Wolman Disease Fibroblasts by Gene Transfer of Lysosomal Acid Lipase" (Feb. 10, 2001) Human Gene Therapy, 12, 279–289.*

(List continued on next page.)

Primary Examiner—Jon P. Weber
(74) Attorney, Agent, or Firm—Frost Brown Todd LLC

(57) ABSTRACT

The present invention comprises a method to diminish and/or eliminate atherosclerotic plaques, in mammals, through direct and indirect treatment of these plaques, in situ, using suitable substances which are capable of lipid removal, primarily through hydrolysis, either by a catalytic or stoichiometric process, wherein the substance targets receptors in and/or on the cell which lead to uptake into the lysosome. Such substances used to diminish and/or eliminate atherosclerotic plaques are generally comprised of lipid hydrolyzing proteins and/or polypeptides.

29 Claims, 4 Drawing Sheets

OTHER PUBLICATIONS

Du et al., "Enzyme Therapy for Lysosomal Acid Lipase Deficiency in the Mouse" (Aug. 1, 2001) Human Molec. Genet., 10(16), 1639–1648.*
Du et al. (Am. J. of Human Gen., 57 (4 SUPPL): p A178 1995).*
Rader et al. (FASEB J., vol. 10, 1996, p. A233).*
Journal of Lipid Research, vol. 40, pp. 397–404, 1999, Escary et al.
J. Biol. Chem. 125:497–509, Folch, J., Lees, M., and Stanley, G.H.S., 1957.
J.Lipid.Res. 14:164–166, Rudel, L.L. and Morris, M.D., 1973.
J.Biol.Chem. 250:8487–8495, Goldstein, J.L., Dana, S.E., Faust, J.R., Beaudet, Al.L., 1975.
Clinical Chem. 21:437–441, Biggs, H.G, Erikson, J.M. and Moorehead,W.R., 1975.
J.Biol.Chem. 256:6304–6310, Chin, J. and Change, T.–Y., 1981.
Meth. Enzymol 98:241–260, Goldstein, J.L., Basu, S., and Brown, M.S., 1983.
Clin.Genet. 26:109–116, Ginsberg, H., Grabowski, G.A., Gibson, J.D., 1984.
Atherosclerosis 62:11, Coates, P.M., Langer, T., and Cortner, J.A., 1986.
Nature 343:425–430, Goldstein, J.L. and Brown, M.S., 1990.
Hospital Practice, 67–78, Magazine article, Dietschy, J.M., 1990.
J.Biol.Chem. 265:22479–22484, Anderson, Richard A. and Sando, Gloria N., 1991.
Proc.Natl.Acad.Sci. USA 90:11603–11607, Hua, S., Yokoyama, C., Wu, J., Briggs, M.R., 1993.
J.Biol.Chem. 268:14497–14504, Wang, X., Briggs, M.R., Hua, X. Yokoyama, C., 1993.
Cell 75:187–197, Yokoyama, C., Wang, X., Briggs, M.R., Admon, A., 1993.
Cell 77:53–62, Wang, X., Sato, R., Brown, M.S., Hua, X., 1994.
J.Biol.Chem. 269:17267–17273, Sato, R., Yang, J., Wang, X., Evans, M.J., , Ho, Y.K., 1994.
J.Clin, Invest. 93:1885–1893, Ishibashi, S., Goldstein, J.L., Brown, M.S., Herz, J., 1994.
J.Biol.Chem. 270:27766–27772, Sheriff, S., Du, H., and Grabowski, G., 1995.
J.Biol.Chem. 270:25578–25583, Bennett, M.K., Lopez, J.M., Sanchez, H.B. and Osborne, 1995.
Crit.Rev.Eukarot.Gene.Expr. 5:317–335, Osborne, T.F., 1995.
J.Lipid.Res. 36:1522–1532, Kirk, E.A., Moe, G.L., Caldwell, M.T., Lernmark, 1995.
Am.J.Hum.Genet 57:1017A, Sheriff, S. and Du, H., 1995.
J.Biol.Chem. 270:27766–27772, Sheriff, S., Du. H., and Grabowski, G.A., 1995.
J.Lipid.Res. 37:937–949, Du, H., Witte, D.P., and Grabowski, G., 1996.
Genes.Dev. 10:1096–1107, Kim, J.B. and Spiegelman, B.M., 1996.
Proc.Natl.Acad.Sci.USA 93:945–950, Ericsson, J., Jackson, S.M., Lee, B.C. and Edwards, P.A., 1996.
Proc.Natl.Acad.Sci.USA 93:1049–1053, Lopez, J.M., Bennett, M.K., Sanchez, H.B., Rosenfeld, 1996.
J.Lipid.Res. 37:2271–2279, Groener, J.E.M., Bax, W., and Poorthuis, B.J.H.M., 1996.
J.Bio.Chem. 272:7298–7305,Ericsson, J., Jackson, S.M., Kim, J.B., Spiegelman, 1997.
Proc.Natl.Acad.Sci. USA 94:12975–12980, Swinnen, J.V., Ulrix, W., Heyns, W., and Verhoeven, 1997.
J.Bio.Chem. 272:20213–20221, Sakai, J., Nohturfft, A., Cheng, D., Ho, Y.K., 1997.
Proc.Natl.Acad.Sci. USA 94:12354–12359, Shimomura, I., Bashmakov, Y., Shimano, H., Horton, 1997.
J.Lipid.Res. 38:1503–1521, Fielding, C.J., and Fielding, P.E., 1997.
Proc.Natl.Acad.Sci. USA 94:12610–12615, Rigotti, A., Trigatti, B.L., Penman, M., Rayburn, H., 1997.
Proc.Natl.Acad.Sci. USA 94:13600–13605, Ternel, R.E., Trigatti, B., DeMattos, R.B., Azhar, S., 1997.
Gene 208:285–295, Du, H., Duanmu, M., and Rosa, L.R., 1998.
Molecular Genetics and Metabolism 64:126–134, Du, H., Sheriff, S., Bezerra, J., Leonova, T., 1998.
Curr.Opin.Lipidol. 9:137–140, Osborne, T.F. and Rosenfeld, J.M., 1998.
Hum.Mol.Gen., Du, H., Duanmu, M., Witte, D.P., and Grabowski, G., 1998.
J.Bio.Chem. 273:5599–5606, Jian, B., Liera–Moyer, M., Ji, Y., Wang, N., Philliops, 1998.
Endocrinology 139:72–80, Johnson, M.S.C., Svensson, P.A., Helou, K., Billig, H., 1998.
J.Bio.Chem. 273:8434–8438, Fluiter, K., Westhuijzen, D.R., and Berkel, T.J.C., 1998.
Biochem.Biophy.Acta. 1389:112–122, Somerharju, P. and Lusa, S., 1998.
Proc.Natl.Acad.Sci. USA 97:5972–5977, Wert, S.E., Yoshida, M., LeVine, A.M., Ikegami, M., 2000.

* cited by examiner

LIPID HYDROLYSIS THERAPY FOR ATHEROSCLEROSIS AND RELATED DISEASES

This application is based on and claims priority from U.S. Provisional Patent Application Ser. No. 60/180,362, Gregory A. Grabowski and Hong Du, filed Feb. 4, 2000.

FIELD OF INVENTION

The present invention relates to the use of lipid dissolving substances for the treatment and prevention of coronary artery disease. More specifically, this invention relates to the use of lipid hydrolyzing proteins and/or polypeptides, such as lysosomal acid lipase (LAL), for the treatment and prevention of atherosclerosis in mammals.

BACKGROUND

The increasing number of patients suffering from atherosclerosis continues to drive research into cholesterol and triglyceride metabolism. Through a large number of investigations, the essentials of the control of cholesterol metabolism have been elucidated in the past two decades (see FIG. 1). The central system for the control of cholesterol metabolism requires two sets of separable pathways: 1) the endogenous pathway and 2) the exogenous cholesterol-entry pathways. Both of sets of pathways are modulated by the protein lysosomal acid lipase (LAL) [1]. In the former, the cell senses the need for endogenous cholesterol synthesis via the release of transcription factors, Sterol Regulatory Element Binding Proteins (SREBP1 and 2), whose precursors are bound to the nuclear membrane and endoplasmic reticulum. SREBPs up-regulate HMG-CoA reductase and other enzymes in the endogenous synthesis pathways [2–5]. This upregulation is derived from the cell's biochemical feedback mechanism sensing a low level of free cholesterol in the surrounding media and/or plasma that is derived from the receptor mediated endocytosis pathway; i.e., the exogenous pathway [6]. Low density lipoprotein receptors (LDLR) and other plasma membrane receptors participate in this uptake process. These LDLR-delivered and other lipoprotein associated lipids are presented to the lysosome for degradation by LAL. Once a deficient exogenous cholesterol supply is sensed, SREBP1 and 2 stimulate the transcription of a cascade of enzymes leading to the production of free intracellular cholesterol and fatty acids [7–10]. The cell then senses the adequacy of free cholesterol levels and, once exceeded, ACAT (acyl CoA: cholesterol acyltransferase) is directly activated by free cholesterol and ACAT synthesis is up regulated. The net effect is to remove free cholesterol by esterification to a cytoplasmic storage pool of cholesteryl esters that is not contained within membranes, i.e., non-lysosomal, and to remove free cholesterol and cholesteryl esters from the cells. Once the cell senses that sufficient free cholesterol is available, a steady state pool of free cholesterol is maintained [11].

Both SREBP1 and 2 are transcription factors that bind to Sterol Regulatory Elements (SREs) in the promoter regions of key genes in cholesterol and fatty acid synthesis. The SREBPs are activated by a two step proteolytic process that is mediated by proteases that are activated by free cholesterol sensing elements in the plasma membrane and, potentially, other components of the cell [12, 13]. These proteases cleave the endoplasmic recticulum (ER) resident SREBPs and release their active components which are then transported to the nucleus. SREBP2 has a single transcript whereas the SREBP-1 gene produces two transcripts and proteins, SREBP-1a and SREBP-1c. These alternative forms of SREBP1 arise from the use of transcription start sites resident in alternative first exons that are then spliced into a common second exon. In humans, the mRNAs for SREBP-1a/-1c also display alternative splicing at the 3' end that leads to proteins that differ by 113 amino acids at the C-terminus [14, 15]. All three SREBP members share the same structural domains indicating their common function [16]. These domains include: 1) the $NH_2$-terminal segment of 480 amino acids is a basic helix-loop-helix-leucine zipper-"like" transcription activator, 2) the middle segment of 80 amino acids comprises two membrane spanning sequences, and 3) the carboxy-terminal half of 590 amino acids that functions as a regulatory domain [17].

There are at least two pathways for the entrance of external cholesterol into monocyte/macrophage derived cells [18]: 1) the ldlr and ldlr-related protein systems [19]; and 2) the scavenger receptor system (e.g., SRA, SR-B and CD36) for lipoprotein bound cholesteryl esters (CE's) [20–24]. The SR-B1 pathway delivers cholesteryl esters into the cell via transfer of cholesteryl esters through SR-B1 without uptake of HDL [25, 26].

In the LDL-CE (cholesteryl ester) or -TG (triglyceride) pathway, the complexes are taken up into cells following receptor-mediated recognition. The endosomal pathway delivers these lipids to the lysosomes after uncoupling the LDL-lipid complexes from the receptor in the late endosomal acidified compartment. Once the LDL-lipid particle is delivered to the lysosome, the lipids are liberated, possible after degradation of the LDL particle, via proteolysis or by simultaneous attack through proteolysis and by LAL [27]. This derived free cholesterol is then transported out of the lysosome into the cytosol by one or more proteins resident in, or at, the lysosomal membrane. Once it exits the lysosome, free cholesterol moves to the inner surface of the plasma membrane and directly to the endoplasmic reticulum. Free cholesterol from the inner surface of the plasma membrane is then transported to the endoplasmic reticulum and participates in the feedback control of the endogenous synthetic pathway. Thus, from this simplified overview of cholesterol and triglyceride metabolism in cells, it is clear that LAL occupies a central position in the control of endogenous cholesterol synthesis since, without its activity, neither free cholesterol nor free fatty acids (FFA) derived from the LDL pathway can be liberated from the lysosome to control these critical pathways.

The importance of LAL in cholesterol and triglyceride metabolism is underscored by the human phenotypes resulting from inherited deficiencies of LAL. These two rare diseases, Wolman Disease and Cholesteryl Ester Storage Disease, are early and late onset diseases, respectively [28]. Wolman disease results in the massive accumulation of cholesteryl esters and triglycerides in lysosomes of a variety of tissues and cells including those of the liver (hepatocytes and Kupffer cells), spleen, adrenal gland and epithelium of the small intestine. This leads to a severe phenotype characterized by hepatosplenomegaly, adrenal calcification, and a thickened and dilated small intestine. In comparison, cholesteryl ester storage disease is a much more heterogeneous disease with onset from early childhood to late adolescence, and even adulthood with isolated hepatomegaly and/or progressive cirrhosis and primarily storage of cholesteryl esters.

The inventor has discovered that additional circumstantial evidence has implicated lower LAL activities in monocytes and/or plaques from patients with atherosclerosis or carotid artery atheromata. This evidence indicates that polymorphic variants could lead to differential activity of LAL in various tissues and may predispose to, or be an additional risk factor in, the development of atherosclerotic disease in humans [29]. In accordance with this invention, this suggests that supplementation of LAL activity in cells of pathologic involvement in athero-/arterio-sclerosis may provide a means to diminish the accumulated, pathologic cholesteryl esters and triglycerides that are causally related to these diseases.

SUMMARY OF THE INVENTION

As described herein, the present invention comprises a method to diminish and/or eliminate atherosclerotic plaques in mammals, through direct and indirect treatment of these plaques, in situ, using proteins and/or polypeptides. These proteins and/or polypeptides are capable of lipid removal, primarily through hydrolysis, either by a catalytic or stoichiometric process, wherein the lipid hydrolyzing protein or polypeptide targets receptors in and/or on the cell leading to uptake into the lysosome. Receptor sites are selected from the group consisting of oligosaccharide recognition receptors and peptide sequence recognition receptors.

Generally, compositions used for practicing this invention include lipid hydrolyzing proteins or polypeptides, and in particular, the protein lysosomal acid lipase (LAL). However, other lipid hydrolyzing proteins or polypeptides may also be used, such as proteins which show at least 85% sequence homology to lysosomal acid lipase or proteins having a $Ser^{153}$ residue. Other proteins include polymorphic variants of lysosomal acid lipase with substitution of amino acid Pro(-6) to Thr and Gly2 to Arg and also polypeptides showing similar biological activity as lysosomal acid lipase.

Exogenously produced lipid hydrolyzing proteins or polypeptides, contained in a pharmaceutically acceptable carrier, may be administered either orally, parenterally, by injection, intravenous infusion, inhalation, controlled dosage release or by intraperitoneal administration in order to diminish and/or eliminate atherosclerotic plaques. The preferred method of administration is by intravenous infusion.

Endogenously produced lipid hydrolyzing proteins and/or polypeptides may also be used to diminish and/or eliminate atherosclerotic plaques. Generally, such a method involves providing a biologically active human lipid hydrolyzing protein or polypeptide, such as human lysosomal acid lipase, to cells of an individual having a deficiency in biologically active human lipid hydrolyzing protein(s) or polypeptide(s). This is accomplished by in vivo administration into cells competent for the production of biologically active human lipid hydrolyzing protein or polypeptide, a vector comprising and expressing a DNA sequence encoding biologically active human lipid hydrolyzing protein or polypeptide. The vector used may be a viral vector, including but not limited to a lentivirus, adenovirus, adeno-associated virus and virus-like vectors, a plasmid, or a lipid vesicle. The vector is taken up by the cells competent for the production of biologically active human lipid hydrolyzing protein or polypeptide. The DNA sequence is expressed and the biologically active human lipid hydrolyzing protein or polypeptide is produced. Additionally, the cells harboring this vector will secrete this biologically active lipid hydrolyzing protein or polypeptide which is then subsequently taken up by other cells deficient in the lipid hydrolyzing protein or polypeptide.

Other proteins and/or polypeptides which may be used for endogenous treatment of atherosclerotic plaques includes biologically active proteins having at least 85% sequence homology to lysosomal acid lipase, polymorphic variant proteins of lysosomal acid lipase with substitution of amino acid Pro(-6) to Thr and Gly2 to Arg and polypeptides showing similar biological activity to lysosomal acid lipase.

The abbreviations for cellular components are as follows: PM=Plasma membrane, ER=endoplasmic reticulum, TGN=trans–Golgi network, MVB multivesicular body, EN=endosome, FC=free cholesterol, FFA=free fatty acid, CYTO CE=re-esterified or esterified non-lysosomal cholesteryl ester (CE), NPC1=site of the Niemann-Pick C1 defect, LAL=lysosomal acid lipase.

Figure 1:
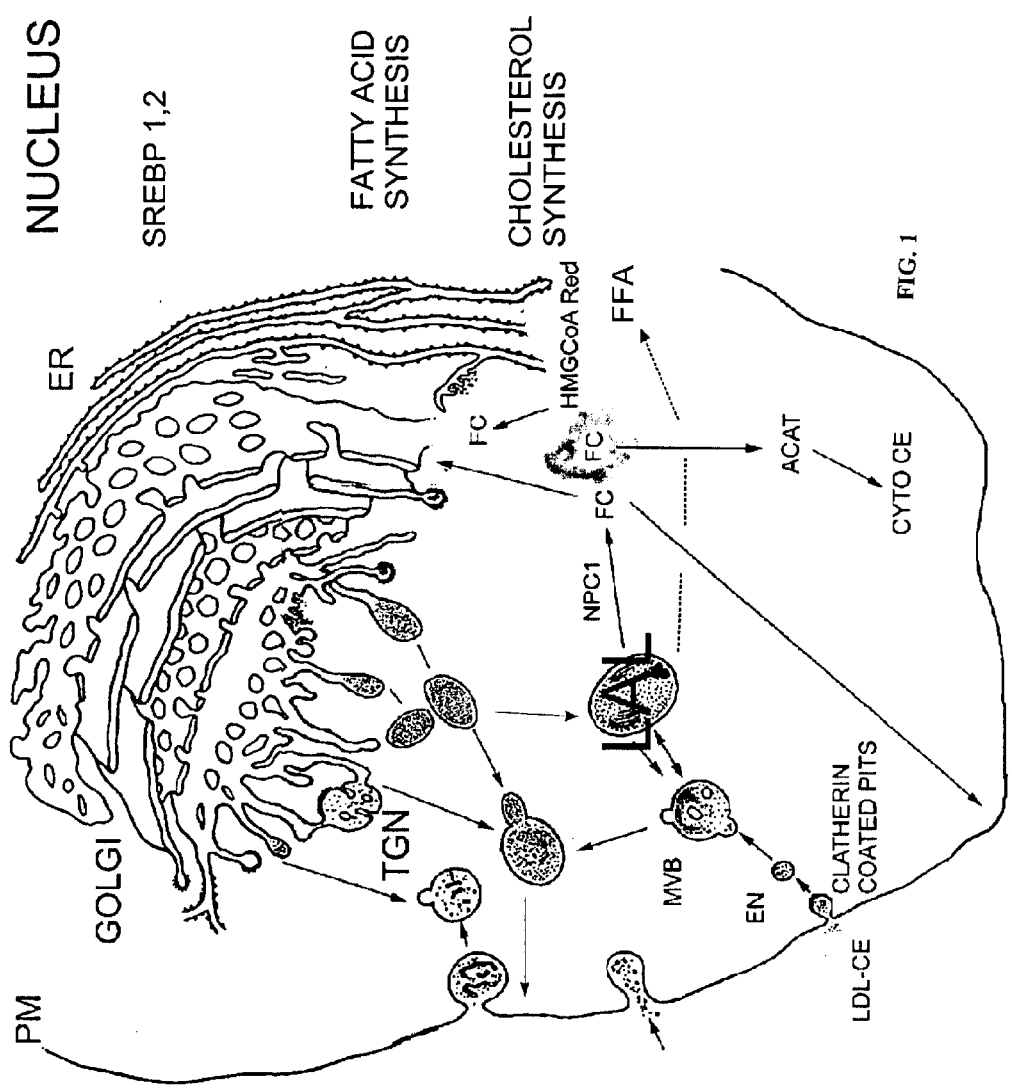
FIG. 1: Schematic of a mammalian cell to illustrate the pathways for cholesterol and fatty acid incorporation into cellular metabolism. Two pathways are illustrated: 1) the endogenous synthesis of cholesterol and fatty acids controlled by the SREBP1 and 2 systems that sense the level of extralysosomal cellular cholesterol as modulated by LAL cleavage of cholesteryl esters and triglycerides in the lysosomes; 2) the exogenous pathway whereby cholesteryl esters and triglycerides enter the cell via receptor mediated endocytosis (shown as LDL-CE as an example) for delivery to the lysosomes inside of the cells. The LDL receptor and several other scavenger receptors participate in this pathway. LAL controls the egress of cholesterol and fatty acids from the lysosomes that enter the cell via this pathway. The liberation of free cholesterol and/or fatty acids by LAL or other such therapeutic compounds leads to a direct effect to reduce cholesterol and FFA synthesis in the cell via the SREBP sensing systems. Reductions in cellular cholesterol and/or FFA can be achieved by this direct effect and/or by removal of the free cholesterol and/or FFA from the cell by transport of cholesterol across the plasma membrane and out of the cell.
Figure 2:
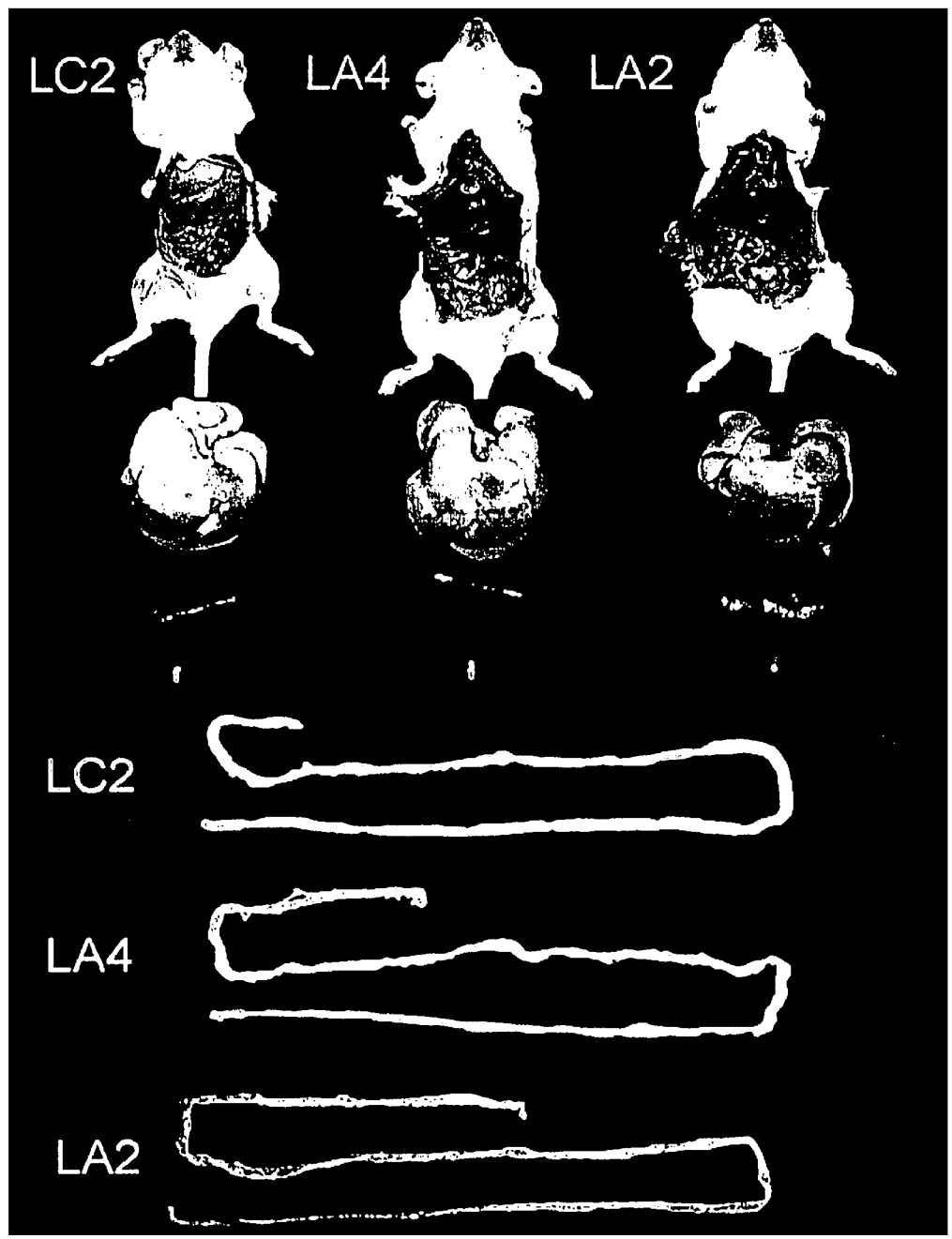

FIG. 2: Typical gross pathology of LAL untreated (LC2) and treated (LA2 and LA4) lal–/– mice: [Top] Ventral views showing the yellow fat-infiltrated lover in a typical (LC2) untreated lal–/– mouse. In treated (LA2 and LA4) lal–/– mice, the livers had essentially normal color. [Middle] Gross appearance of liver (top), spleen (middle) and kidney (bottom) from LC2, LA4 and LA2 mice. The untreated mouse spleen is lighter than that from the treated mice spleens. [Bottom] Gross appearance of the small intestine from untreated LC2 and treated LA4 and LA2 mice. The small intestine of untreated mouse (LC2) gives a lighter appearance, indicating build-up of cholesterol and triglycerides. This is in contrast to the darker intestines shown for the treated mice (LA4 and LA2).

Figure 3:
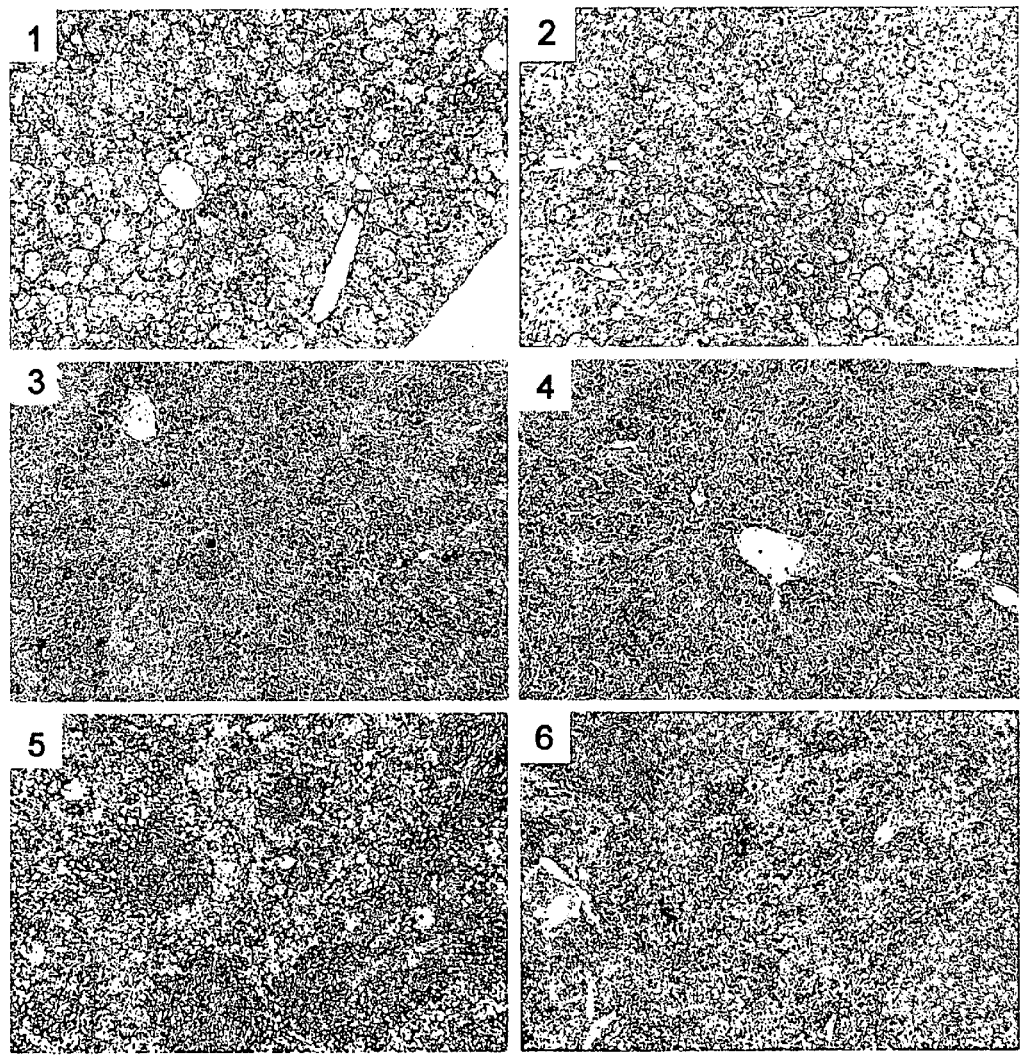

FIG. 3: Light microscopy of the liver, spleen and small intestine from LAL untreated (LC2) and treated (LA2) lal– mice. H & E stained sections from liver (3A and 3B), spleen (3E and 3F). Stained frozen sections from liver (3C and 3D). A, C, E, (left) are from untreated lal–/– mice. B, D, and F (right) are from LAL treated mice. Treated mice had substantially diminished macrophage storage cell numbers compared to those in untreated mice. The staining indicates large accumulations of neutral fat in livers from untreated mice and their large decrease to near absence in liver.

Figure 4:
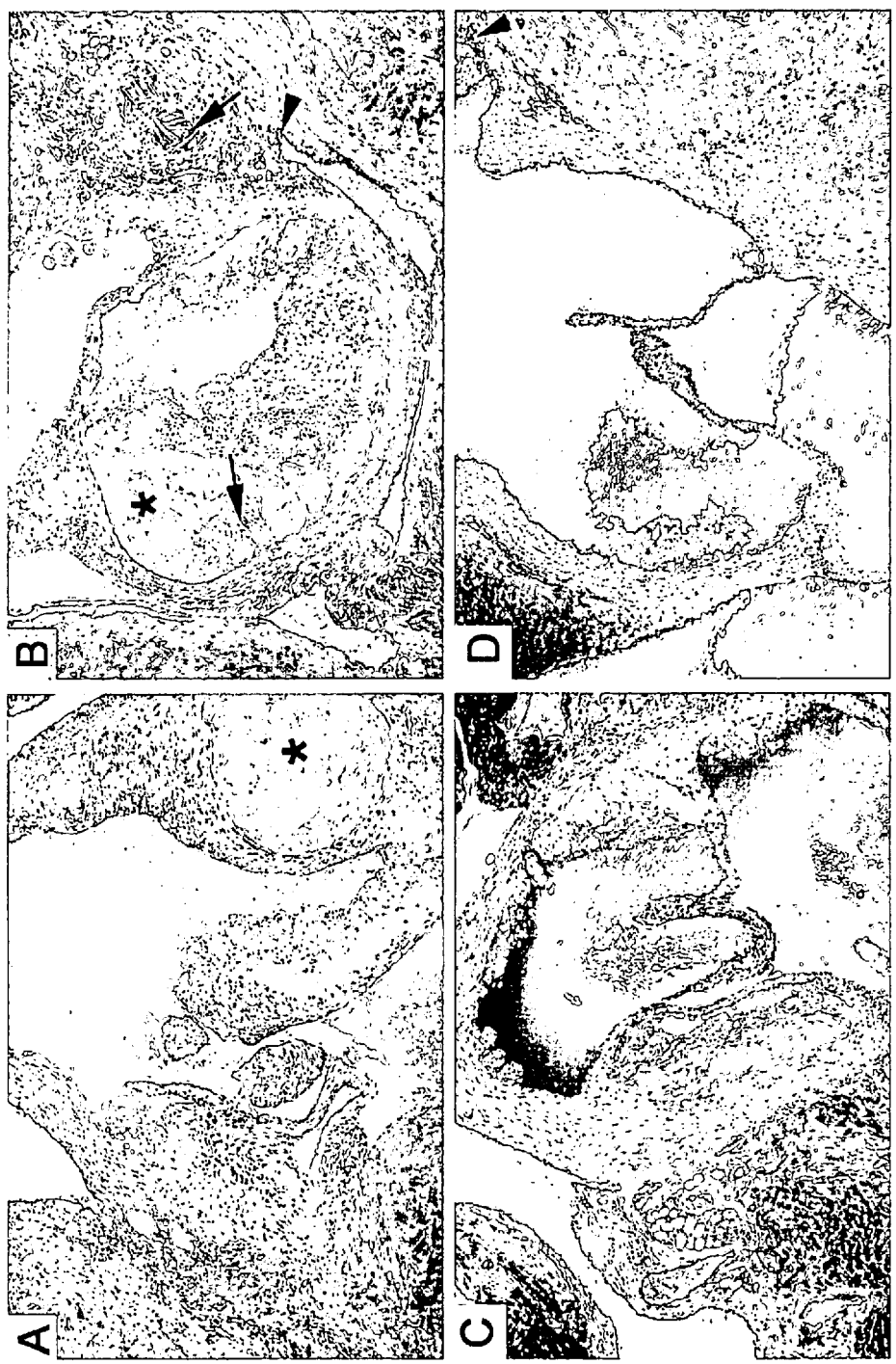

FIG. 4: Representative sections from the aortic valve of ldlr–/– mice with or without LAL treatment stained with H & E. (A nd B) Typical foamy cell-rich fatty streaks in 3.5 month old ldlr–/– mice on HFCD for 2 months. The asterisk indicates a necrotic zone next to disrupted medial layer. The arrows point to cholesterol clefts/crystals. The arrow on the right (cholesterol clefts/crystals) show a coronary artery near the ostium. (C) Reduced foamy cells in the fatty streaks of the aortic valve of the LAL treated mice. This was from the most involved LAL treated mouse. (D) A typical example (3/5) of the normal aortic valves from LAL treated mice.

DETAILED DESCRIPTION OF THE INVENTION

Definitions

The terms "amino acid" or "amino acid sequence," as used herein, refer to an oligopeptide, peptide, polypeptide, or protein sequence, or a fragment of any of these, and to naturally occurring or synthetic molecules. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

As used herein, the term "exogenous lipid hydrolyzing proteins or polypeptides" refers to those produced or manufactured outside of the body and administered to the body; the term "endogenous lipid hydrolyzing proteins or polypeptides" refers to those produced or manufactured inside the body by some type of device (biologic or other) for delivery to within or to other organs in the body.

As used herein, the term "biologically active" refers to a protein having structural, regulatory, or biochemical functions of a naturally occurring molecule.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological function of the natural molecule. A derivative polypeptide is one modified, for instance by glycosylation, or any other process which retains at least one biological function of the polypeptide from which it was derived.

The words "insertion" or "addition," as used herein, refer to changes in an amino acid or nucleotide sequence resulting in the addition of one or more amino acid residues or nucleotides, respectively, to the sequence found in the naturally occurring molecule.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, or to any DNA-like or RNA-like material. In this context, "fragments" refers to those nucleic acid sequences which, when translated, would produce polypeptides retaining some functional characteristic, e.g., lipase activity, or structural domain characteristic, of the full-length polypeptide.

The phrases "percent identity" or "percent homology" refers to the percentage of sequence similarity found in homologues of a particular amino acid or nucleic acid sequence when comparing two or more of the amino acid or nucleic acid sequences.

The term "atherosclerosis" refers to the pathologic processes that leads to abnormal accumulation of cholesterol and cholesteryl esters and related lipids in macrophages, smooth muscle cell and other types of cells leading to narrowing and/or occlusion of one or several arteries and arterioles of the body and bodily organs, including but not limited to, the coronary arteries, aorta, renal arteries, corotid arteries, and arteries supplying blood to the limbs and central nervous system. The associated inflammatory reactions and mediators of this pathologic process also are included in this definition.

The term "atherosclerotic plaque" refers to the build up of cholesterol and triglycerides due to atherosclerosis.

Discussion

The consequences of atherosclerosis are a leading cause of mortality and morbidity. Macrophages that accumulate cholesteryl esters are known to be a major component contributing to the build-up of atherosclerotic plaques in coronary arteries as well as the carotid arteries, the aorta and other peripheral vessels throughout the body. These cholesteryl esters are derived from the circulation where they are carried on lipoproteins. The cholesteryl esters enter cells via low-density lipoprotein receptors (LDL-R) and other scavenger receptors for oxidized low-density lipoprotein (LDL) particles. Once internalized, these particles and their attached cholesteryl esters are delivered to the lysosome for cleavage to cholesterol by lysosomal acid lipase (LAL).

Current therapeutic approaches for treating atherosclerosis include dietary manipulation (low cholesterol diets) and exercise, cholesterol synthesis inhibitors and surgical coronary artery by-pass. However, dissatisfaction with the success of these interventions provides the impetus for continued development of new/alternative/adjunctive therapies for this major disease group.

There are two primary methods employed for the treatment of atherosclerosis and the dissolution of atherosclerotic plaque. The first method of treatment is coronary by-pass surgery. This method is used to treat patients with established, unstable angina and/or progressive angina. The second method of treatment is chemical inhibition of hepatic cholesterol synthesis using the class of drugs termed "statins." This approach inhibits the synthesis of cholesterol by inhibiting the action of the rate-limiting enzyme, HMG-CoA reductase, in the cholesterol synthetic pathway. Coronary artery by-pass surgery is effective in diminishing angina attacks of selected patients and the statins have been shown to successfully lower plasma cholesterol and diminish the propensity to develop atherosclerotic plaques. However, neither approach offers the potential for direct dissolution of existing atherosclerotic plaques.

LAL represents the major biochemical pathway of cholesteryl ester entry into the body, and is subsequently used to modulate cellular cholesterol biosynthesis. Once LAL liberates cholesterol from cholesteryl esters, the free cholesterol exits the lysosome and leads to the sterol regulatory element binding protein (SREBP) mediated down regulation of cholesterol synthesis. The accumulation of cholesteryl esters within the macrophages of atherosclerotic plaques occurs in the presence of normal amounts of LAL. This fact indicates that the delivery of cholesteryl esters to these cells exceeds the capacity of normal amounts of LAL to catabolize the delivered cholesteryl esters that initiate the development of atherosclerotic plaques. This process disrupts normal cellular metabolism for the regulation of endogenous cellular cholesterol synthesis and leads to excess amounts of cholesterol and cellular cholesteryl ester synthesis via the lack of down regulation of the SREBP-mediated system of cholesterol synthesis and the acyl CoA: cholesterol acyltransferase (ACAT) pathway for intracellular cholesteryl ester synthesis [30].

Similar events occur in the liver, which is the major organ in the body responsible for cholesterol biosynthesis and for maintenance of cholesterol homeostasis. Delivery of LAL to hepatocytes in excess of normal amounts enhances the egress of free cholesterol from the lysosome (i.e., increases the flux of cholesteryl esters through the lysosomal system) that is a major pathway for the metabolism of such lipids delivered to hepatocytes from the portal circulation and the diet. The result is an increase in cholesterol liberated from lysosomes, which subsequently down modulates hepatic cholesterol synthesis and its supply to the body. This diminishes the load of cholesterol and cholesteryl esters to peripheral sites thereby lowering the atherogenic potential.

The use of a suitable protein or polypeptide, such as LAL or a homologue of LAL possessing similar biological activity, offers an alternative means of therapy for atherosclerosis as well as peripheral vascular disease. LAL functions by preventing the progression or promoting the regression of atherosclerotic plaque legions via two mechanisms: 1) by directly entering the lesional foam cells and enzymatically dissolving the stored cholesteryl esters as well as tri-, di-, and mono-acylglycerides; and 2) by indirectly promoting lysosomal egress of free cholesterol and free fatty acids that could modulate cellular (hepatic, macrophage and other) lipid synthesis mediated by the SREBP or other pathways. Patients who suffer from atherosclerosis have a tendency to have decreased levels of LAL in the atheromatous plaques.

LAL, a member of the lipase family, is a 372 amino acid glycoprotein that is trafficked to the lysosome via the mannose receptor system [31–33]. The cDNA sequence which encodes LAL has been previously reported [34]. This glycoprotein has six glycosylation consensus sequences (Asn-X-Ser-/Thr) and three at $Asn^{15}$, $Asn^{80}$ and $Asn^{252}$ are conserved among members of the lipase gene family. All members of the lipase gene family have conserved GXSXG pentapeptide sequences that contain the active site serine nucleophiles [35–37]. LAL has two such sequences at residues 97–101 and 151–155 with potential serine nucleophiles at residues 99 and 153, where a key nucleophile resides at the Ser 153 residue. LAL cleaves cholesteryl esters and triglycerides in vitro using phospholipid/detergent systems. $Ser^{53}$ has been defined as a part of the Asp-Ser-His catalytic triad common to many lipases.

Suitable lipid hydrolyzing substances for use in this invention include, but are not limited to, glycoproteins such as LAL, homologues of LAL, wherein the homologues possess at least 85% sequence homology, due to degeneracy of the genetic code which encodes for LAL, polypeptides possessing similar biological activity to LAL and non-peptide derived substances. Also included are lipid hydrolyzing proteins and polypeptides which contain the catalytic lipase triad Asp-Ser-His, where the Ser is a $Ser^{153}$ residue. Additional substances include polymorphic variants of LAL in which two of the amino acids are replaced with different amino acids. An example of such polymorphic variants are prepared by cloning LAL from normal human liver cDNA library and changing two nucleotides (C86 to A and G107 to A) which results in substitution of amino acid Pro(-6) to Thr and Gly2 to Arg in LAL, yielding four different polymorphic variants of LAL. Additional amino acid sequences include those capable of lipid hydrolysis, either catalytic or stoichiometric, wherein the residue 153 of the amino acid chain is a serine residue.

Further LAL-derived proteins include those proteins having the native LAL sequence, but which have more than six N-linked acetylglycosylation residues or fewer than six N-linked acetylglycosylation residues. Each glycosylation site has two N-linked acetylglucosamine residues, which are oligosaccharide-terminated, where the oligosaccharide-terminating residue is preferably an α-mannose residue and where there are at least three oligosaccharide-terminating residues at each glycosylation site.

For the treatment of atherosclerosis, the lipid hydrolyzing substance targets receptors which lead to uptake into the lysosome. These receptors include but are not limited to the categories of oligosaccharide recognition receptors, which includes the mannose receptor, the mannose-6-phosphate receptor and the category of peptide sequence recognition receptors, which includes CD 36 and LDL receptors.

Methods of Treatment of Atherosclerosis Using Lipid Hydrolyzing Amino Acid Sequences LAL could be used in conjunction with statins to reduce the level of artherosclerotic plaques. Additionally, LAL could also be used in conjunction with by-pass surgery for some patients who develop restenosis and/or to prevent redevelopment of plaques following surgery. In addition, treatment with therapeutic agents, such as LAL, can effect beneficial improvements in arteries and/or arterioles that cannot be accessed by surgical or other such invasive approaches. Additional advantages of LAL treatment may include the elimination of the need for surgery in some patients and supplying a natural product to patients without the attendant or potential side effects of synthetic chemicals, as is the case for the statin therapy approach.

LAL therapy can also be used for the treatment of two rare human diseases, Wolman Disease and Cholesteryl Ester Storage Disease. Both of these diseases are due to mutations at the LAL locus. The former leads to death in the first year of life and the latter is a prolonged disease with development of cirrhosis of the liver in later life. Neither disease currently has therapy regimes available.

Additional potential therapeutic roles for LAL treatment include its use in the treatment of fatty liver of pregnancy, unspecified fatty infiltration of the liver, peripheral atherosclerotic disease due to secondary diseases such as diabetes mellitus, carotid stenosis due to atherosclerosis, and similar disease states.

The lipid hydrolyzing protein or polypeptide can be used therapeutically either as an exogenous material or as an endogenous material. Exogenous lipid hydrolyzing proteins or polypeptides are those produced or manufactured outside of the body and administered to the body. Endogenous lipid hydrolyzing proteins or polypeptides are those produced or manufactured inside the body by some means (biologic or other) for delivery to within or to other organs in the body. LAL is present in body tissue. Patients who suffer from atherosclerosis have a tendency to have decreased levels of LAL in the atheromatous plaques. In order to achieve such desired results for both direct and indirect treatment of the plaques, the lipid hydrolyzing protein or polypeptide targets specific organs via specific receptors. For example, LAL can target the mannose receptor systems, or other oligosaccharide specific receptors and enters macrophages, smooth muscle cells, endothelial cells and hepatocytes.

Endogenous Therapy:

An indirect treatment of plaques involves supplying LAL to the major organs of cholesterol biosynthesis, primarily the liver. This leads to a greater net lysosomal throughput of cholesteryl esters and delivery of free cholesterol to the cytoplasm, where overall cholesterol synthesis would be diminished. It also results in a reduction of the endogenous supply of cholesterol from the liver to peripheral organs, i.e. macrophages in developed or developing plaques.

The principles of gene therapy for the production of therapeutic products within the body include the use of delivery vehicles (termed vectors) that can be non-pathogenic viral variants, lipid vesicles (liposomes), carbohydrate and/or other chemical conjugates of nucleotide sequences encoding the therapeutic protein or substance. These vectors are introduced into the body's cells by physical (direct injection), chemical or cellular receptor mediated uptake. Once within the cells, the nucleotide sequences can be made to produce the therapeutic substance within the cellular (episomal) or nuclear (nucleus) environments. Episomes usually produce the desired product for limited periods whereas nuclear incorporated nucleotide sequences can produce the therapeutic product for extended periods including permanently.

Such gene therapy approaches are used to produce therapeutic products for local (i.e., within the cell or organ) or distant beneficial effects. Both may provide decreases in pathologic effects and may combine to produce additive and/or synergistic therapy. For either effect, local or distant, the natural (termed normal) or altered (mutated) nucleotide sequences may be needed to enhance beneficial effects. The latter may be needed for targeted delivery to the specific cellular type involved in the pathology of the disease. For atherosclerosis distant delivery would be needed to macrophages (foam cells), smooth muscle cells and other various cell types within the pathologic lesions, known as atheromata. Subcellular delivery to the lysosomes may also be necessary and variants made available or produced for such an approach.

An approach for the use of lipid removal substances, particularly lipid hydrolyzing proteins and polypeptides for the treatment of atherosclerosis and removal of atherosclerotic plaques, can be achieved by the gene therapy approaches discussed above. Such approaches provide a source of a biologically active human lipid hydrolyzing protein or polypeptide for delivery into the body by biologic or other production systems. This method of introduction can be achieved by internal or production sources (biologic or other, gene therapy vectors, liposomes, gene activation etc.) which lead to the production of biologically active human lipid hydrolyzing proteins and polypeptides by certain cells of the body. The source may provide for the local or distant supply by, for example, direct effects within the cell or by secretion out of the cells for delivery to other cells of the body, like those in atheromatous plaques. This includes, but is not limited to, somatic gene therapy approaches that would allow for the synthesis and/or otherwise production of the therapeutic substance in the body. In particular, nucleotide sequences encoding the functional, lipid hydrolyzing, sequences of the lysosomal acid lipase incorporated into conjugates, liposomes, viral (i.e., lentivirus, adenovirus, adeno-associated virus or other viruses or such virus-like vectors) vectors for expression of the active sequences for therapeutic effect. In addition, nucleotide sequences encompassing the functional components of biologic and therapeutic interest and residing in the body's cells could be made to produce, express or otherwise make the requisite compound in therapeutic amounts. The therapeutic lipid hydrolyzing protein or polypeptide, thus produced in the body, would lead to a reduction or elimination of the atheromatous plaques or other lesions of atherosclerotic plaques.

Variants and homologous nucleotide or encoded sequences of human lysosomal acid lipase incorporated for synthesis and/or production of the active protein/peptide are transiently or permanently integrated into cells for therapeutic production. The normal, polymorphic variants, specifically mutated or modified lysosomal acid lipase sequences may be expressed from the context of the vectors incorporated into cells for normal and/or specifically modified function to enhance or otherwise promote therapeutic effects.

Such sequences can lead to the in vivo synthesis of the desired biologically active human lysosomal acid lipase or other therapeutic proteins within cells after incorporation into cells by various routes as described above. Once within cells, the synthesized biologically active human lysosomal acid lipase or another therapeutic protein hydrolyzes cholesteryl esters and/or triglycerides within the lysosomes following their targeted delivery. The resulting release of free cholesterol from the lysosomes leads to down regulation of the endogenous cholesterol synthetic pathway via the SREBP controlled systems. Additionally, human lysosomal acid lipase or other therapeutic human proteins or polypeptides produced from incorporated nucleotide sequences are secreted from cells, enter the circulatory system and are taken up by distant cells via receptor mediated endocytosis or other such lysosomal delivery systems to the lysosomes of pathologically involved cells of the atheromatous plaques. Such plaques include but are not limited to macrophages and smooth muscle cells. Lysosomal liberation of free cholesterol within such cells has at least two beneficial effects on atheromatous plaque reduction and/or elimination: 1) free cholesterol exits from the lysosome and participates in the SREBP mediated down regulation of endogenous macrophage or other cell type cholesterol synthesis, and 2) free cholesterol exits from the lysosome and exits the cell by reverse cholesterol transport. Both effects are beneficial in reducing the amount of accumulated cholesteryl esters within lysosomes of foam cell macrophages and/or other cells of the atheromatous lesions.

The gene vectors containing the requisite nucleotide sequences or other components necessary for therapeutic expression are introduced into the body's cells by several routes as described above and also their direct introduction into atheromatous plaque cells using delivery by angiographic device.

Endogenous therapy also contemplates the production of a protein or polypeptide where the cell has been transformed with a genetic sequence that turns on the naturally occurring gene encoding the protein, i.e., endogenous gene-activation techniques.

Exogenous Therapy:

A method for the direct treatment of atherosclerotic plaques involves supplying LAL to the plaques and the macrophages, and smooth muscles cells therein, so that the cholesteryl esters and/or triglycerides, which are stored or accumulated within lysosomes of these cells, are degraded and eliminated. This subsequently results in the liberation of cholesterol from the lysosomes and a decrease in endogenous cholesterol synthesis within the foam cells (macrophages and smooth muscles cells). The net effect is to reduce the amount of cholesterol accumulating directly in the target site of pathology and to diminish the size of the plaques and other such legions in situ.

It should be noted that the direct and indirect targeting of the plaques are not mutually exclusive and may be synergistic with both local and global effects on cholesterol homeostasis and the diminution of atherogenic potential.

The lipid hydrolyzing proteins or polypeptides useful in the present invention for exogenous therapy may be administered by any suitable means. One skilled in the art will appreciate that many suitable methods of administering the compound to a host in the context of the present invention, in particular a mammal, are available, and, although more than one route may be used to administer a particular protein or polypeptide, a particular route of administration may provide a more immediate and more effective reaction than another route.

Formulations suitable for administration by inhalation include aerosol formulations placed into pressurized acceptable propellants, such as dichlorodifluoromethane, propane, nitrogen, and the like. The active agent may be aerosolized with suitable excipients. For inhalation administration, the composition can be dissolved or dispersed in liquid form, such as in water or saline, preferably at a concentration at which the composition is fully solubilized and at which a suitable dose can be administered within an inhalable volume.

Formulations suitable for oral administration include (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms may include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers.

Formulations suitable for intravenous infusion and intraperitoneal administration, for example, include aqueous and nonaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carriers for example, water, for injections, immediately prior to use. Extemporaneous injection solutions and suspensions can be prepared for sterile powders, granules, and tablets of the kind previously described.

Parenteral administration, if used, could also be by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, Higuchi, issued 1973, which is incorporated by reference herein.

The appropriate dosage administered in any given case will, of course, vary depending upon known factors, such as the pharmacodynamic characteristics of the particular protein or polypeptide and its mode and route of administration; the age, general health, metabolism, weight of the recipient and other factors which influence response to the compound; the nature and extent of the atherosclerosis; the kind of concurrent treatment; the frequency of treatment; and the effect desired.

A preferred method of treating mammals possessing atherosclerotic plaque involves introduction of suitable lipid hydrolyzing protein or polypeptide by intravenous infusion of a safe and effective amount of a lipid hydrolyzing protein or polypeptide, so as to cause the diminution and elimination of the plaque. A safe and effective amount of the lipid hydrolyzing protein or polypeptide is defined as an amount, which would cause a decrease in the level of atherosclerotic plaques in a patient while minimizing undesired side effects. An experienced practioner, skilled in this invention would have knowledge of the appropriate dosing ratios. The activity level of the lipid hydrolyzing protein or polypeptide must also be considered in determining the number of units to administer to achieve the desired effect. Thus, the activity level of the lipid hydrolyzing protein or polypeptide should be sufficient to cause a reduction in atherosclerotic plaques within a reasonable dosage administered.

EXPERIMENTAL EXAMPLES

Study Design

This study was designed for age-matched cohorts of lysosomal acid lipase deficient, lal-/- or low density lipoprotein receptor deficient, ldlr-/-, mice as an open-label, controlled trial of treated and untreated mice. A single dose of LAL was used in all mice. All mice were sacrificed after 30 days of LAL administration. LAL was given as an i.v. bolus via tail vein every third day for 30 days. The cohorts were divided into equal groups for injections on alternate days. Injections were begun at 2.0 or 2.5 months of age for the lal-/- or ldlr-/- mice, respectively. The overall study design is presented in Table 1. The lal-/- mice received a regular chow diet throughout the entire study period. LAL dosing was begun at 2 months of age. The ldlr-/- mice were maintained on a regular chow diet for 1.5 months and then placed on a high cholesterol diet (7.5% fat; 1.25% cholesterol). The LAL dosing was started after the ldlr/1- mice had been on the high fat/high cholesterol diet for 30 days; i.e., at 2.5 months of age. Doses of LAL in the treated groups were 1.48 U (21 $\mu$g; 70 $\mu$l) LAL in 1×PBS with 2% human serum albumin and 10 mM of dithiothreitol (DTT). The control groups received 1×PBS with 2% HSA and 10 mM of DTT. The final cohort was the lal-/-; ldlr-/- combined deficiency.

The mice avidly consumed the high fat/high cholesterol diet and tolerated the injections well. All injections (325) were successful with i.v. administration obtained for all. One ldlr-/- mouse died just prior to initiating the injections. The high mortality in the lal-/-; ldlr-1- mice was due to massive small bowel infarction possibly secondary to vessel blockage from massive macrophage infiltration of the submucosa and lamina propria. The data from these latter double homozygotes: are not included here.

Samples for plasma lipid determinations and antibody analyses were obtained at 32 days after the first injection. All mice were sacrificed 48 h after the final LAL injection.

TABLE 1

Study Design

| Name | Genotype | Diet | # of mice | Age* (mos.) | Injection | Dosage** *(U) | Total Injections |
|---|---|---|---|---|---|---|---|
| LC | lal-/- | chow | 5 | 2 | PBS** | 0 | 10 |
| LA,LB | lal-/- | chow | 8 | 2 | LAL | 1.48 | 10 |
| RC | ldlr-/- | HF/HCh | 4 | 2.5 | PBS | 0 | 10 |
| RA,RB | ldlr-/- | HF/HCh | 8 | 2.5 | LAL | 1.48 | 10 |

TABLE 1-continued

Study Design

| Name | Genotype | Diet | # of mice | Age* (mos.) | Injection | Dosage** *(U) | Total Injections |
|---|---|---|---|---|---|---|---|
| LRC | lal-/-/ldlr-/- | HF/HCh | 4 | 2.5 | PBS | 0 | 10 |
| LRA,LRB | lal-/-/ldlr-/- | HF/HCh | 8 | 2.5 | LAL | 1.48 | 10 |

*The age refers to that at beginning of injections.
**The control injection was 1 X PBS, with 2% HSA and 10 mM DTT.
*** Doses were given every third day to each mouse. 1.48U = 21 µg.

Stability of LAL Activity

The stability of LAL activity at 4° C. was monitored every 3–4 days for 34 days. The LAL activities remained relatively stable over this period of time, although rigorous standardization of the assay remains to be accomplished.

General Methods

Animals. The mice were provided care in accordance with institutional guidelines and all procedures received prior approval by the IACUC at the Children's Hospital Research Foundation, Cincinnati, Ohio. The lal–A mice originated from mixed genetic backgrounds of 129Sv and CF-1. The ldlr–/– mice were purchased from Jackson Laboratory and were cohorts of C57BL6/J. Mice were housed in microisolation, under 12 h/12 h, dark/light cycles. Water and food, regular chow diets or HFCD, were available ad libitum. The mice were genotyped by PCR-based screening of tail DNA.

Plasma lipid analyses. Blood was collected from the inferior vena cava (IVC) of mice after they had been anesthetized with 200 µl triple sedative (Ketamine, Acepromazine, and Xylazine). Plasma was collected after centrifugation (5,000×g; 10 min; 4° C.) of blood and stored at −20° C. Total plasma free cholesterol was determined colorimetrically with a COD-PAP kit (Wako Chemicals). Total plasma, triglycerides were determined in plasma samples with a Triglycerides/GB kit (Boehringer Mannheim). Total plasma cholesterol was determined using a Cholesterol/HP kit (Boehringer Mannheim).

Tissue Lipid analyses. Total lipids were extracted from liver, spleen and small intestine by the Folch method (Folch, J., Lees, M., and Sloane-Stanley, G. H. (1957) A simple method for the isolation and purification of total lipids from animal tissue. *J. Biol. Chem.*, 226, 497–505). Triglyceride concentrations were measured using chemical analysis developed by Biggs. Briefly, both standards and samples in chloroform were evaporated under vacuum. The lipids were resuspended into the following reagents in order: 0.5 ml of isopropanol, 4.5 ml of $H_2O$: isopropanol: 40 mM $H_2SO_4$ (0.5: 3.0: 1.0) and 2.0 ml of Heptane, and mixed by vigorous agitation at each step. The tubes were left to biphase (~5 minutes). In a set of new tubes, 80 mg of florisil was added and 1.0 ml of the upper phase from each sample was transferred into tubes that contained florisil and mixed by agitation. Then, 0.2 ml of this upper phase was transferred to a new set of tubes and 28 mM sodium alkoxide (2.0 ml) was added and mixed carefully. The tubes were incubated at 60° C. for 5 min. Sodium metaperiodate (3 mM, 1 ml) was added to each tube and mixed well. The tubes were left to oxidize for 45 minutes. Finally, 1.0 ml of 73 mM acetyl acetone was added to each tube and incubated at 60° C. for 20 min. The tubes were cooled at room temperature (~25 min), read at 410 nm on a Beckman DU640 spectrophotometer.

Total tissue cholesterol concentrations were measured using the O-phthalaldehyde. Briefly, cholesterol standards and Folch extracted samples were evaporated under $N_2$. O-phthalaldehyde (3 ml, Sigma) was added to each cholesterol standard and tissue sample and mixed. Concentrated sulfuric acid (1.5 ml) was added slowly and, then, mixed and cooled for 5–10 min, and read at 550 nm in a Beckman DU640 spectrophotometer.

Western blot analysis and LAL activity assay: Immunoblots were conducted with anti-LAL antiserum as described. LAL activities were estimated with the fluorogenic substrate, 4-MU-oleate (4-MUO). All assays were conducted in duplicate. Assays were linear within the time frame used and less than 10% of substrates were cleaved.

Histological Analyses. Light microscopic examinations of the livers, spleen, intestine, adrenal glands, kidneys, heart, lung, thymus, pancreas, and brain were performed. The sections were stained with hematoxylin/eosin (paraffin embedded) or Oil red-O (ORO) (frozen sections) for light microscopic analysis.

Immunohistochemical staining. Immunohistochemical analyses were with paraffin-embedded liver sections and were performed with rabbit anti-LAL antibody. The endogenous peroxidase activity was saturated by incubation in methanol containing 0.5% $H_2O_2$ for 10 min.

The primary antibody (1:200) was incubated at 40° C. for overnight. The sections were then washed with 1×PBS three times (5 min per wash), incubated with alkaline phosphatase-conjugated IgG as secondary antibody for 30 min at room temperature, and washed with 1×PBS for 5 min. The signal was detected using VECTASTAIN ABC-AP kit (Vector) and counter stained with Nuclear Fast Red.

LAL uptake studies in J774E and J774A. I macrophage cultures: J774E and J774A.1 cells were maintained in DMEM medium with 60 µM of 6-Thioguanine or in DMEM medium, respectively, supplemented with 10% fetal calf serum, penicillin and streptomycin (37° C.; 5% $CO_2$). For the uptake studies, cells were seeded at $2 \times 10^5$ per well one day before adding LAL or Ceredase. At designated postincubation times, cells were washed with 1×PBS twice, collected with a rubber policeman, and centrifuged (12,000 rpm, 1 min.) at room temperature. The intracellular proteins were extracted by cell lysis with 1% taurocholate/1% Triton X-100, frozen/thawed five times (dry ice and 37° C. water bath), and centrifuged (12,000 rpm, 10 min.) at 4° C. The protein extracts were analyzed by Western blot.

For immunofluorescence staining, cells ($1.5 \times 10^5$) were seeded on chamber slide, incubated with LAL for 5, 18 or 24 hrs, washed with PBS twice, and fixed with 2% Paraformaldehyde for 1 hr. Immunofluoresence staining was performed.

Results

1) Reduction of lipid storage in liver, spleen, and small intestine of lal–/– mice following LAL treatment.

a. Phenotypic and Gross Pathologic Changes (FIG. 2): In lal–/– mice, treatment with LAL resulted in significant correction of lipid storage phenotypes in various organs. At 3 months of age, untreated lal−/− mice developed a yellow/white creamy color to the liver and significant hepatosplenomegaly was present. In comparison, the LAL treated mice had livers and spleens with much more normal colors. The normal livers in age matched controls were about 5% of body weight whereas the livers were 14% in the untreated lal−/− mice. LAL administration decreased this by about 30% (p=0.0029). The splenic weights were similar in the untreated and treated lal−/− mice (p=0.5044). However, the color of the spleen reverted to near normal in the treated group. The small intestine in untreated lal−/− mice was yellow in the duodenum and creamy white in the jejunum. In the treated group, the small intestine partially reverted to a normal color.

b. Histologic Evaluation: H & E or Oil-Red-O staining of liver, spleen and small intestine from untreated and treated mice showed clear differences. In liver, the LAL treated lal−/− mice had reductions in the size and number of lipid filled Kupffer cells (see FIGS. 3A and B). Hepatocytes have less lipid storage than Kupffer cells in untreated lal−/− mice and this hepatocyte storage appeared unchanged in the treated group. Using Oil-Red-O staining for neutral lipids, a significant difference between the livers of the treated and untreated mice was apparent (see FIGS. 3C and D). In the spleen, the treated group showed a reduction in lipid storage cells compared to those present in untreated mice. In the small intestine, the Oil-Red-O staining of LAL treated and untreated mice showed substantial differences. The sections of intestine from untreated mice were full of Oil-Red-O staining cells (macrophages) in lamina propria while comparable sections from treated mice were almost completely negative for Oil-Red-O staining. The aortic arches, aortic base and valves, and coronary arteries of lal−/− mice, treated or untreated, were essentially normal throughout the study.

c. Immunohistochemistry: Immunohistologic analyses of liver with anti-LAL (*E. coli* produced recombinant hLAL) showed predominantly dark staining (positive) of the sinusoidal lining cells. Some antigen could be detected in the storage cells, but this signal was at a low level due to the very large dilution space presented by these cells. The samples of liver were obtained 30 min. after injection. The uninjected lal−/− mice had undetectable lal.

d. Biochemical Findings: Tissue cholesterol (both free and esterified) and triglycerides from liver, spleen and small intestine were determined by chemical analyses. Compared to age matched wild-type mice, the lal−/− mice have elevated cholesteryl esters and triglycerides in several tissues. The average total cholesteryl ester per organ at 3.5 months of age was increased 31-fold in liver and 19-fold in spleen compared to wild-type. LAL administration to such mice was associated with reductions of total cholesterol by 47% in total liver (267.22±8.22 mg vs. 144.23±7.99 mg; p=0.0003, n=3) and by 69% in total spleen (8.73±0.43 mg vs. 2.63±0.50 mg, p=0.0008, n=3). Similar decreases of triglycerides also were observed: 58% in total liver (26.52±17.93 mg vs. 39.79±6.38 mg, p=0.047, n=4) and 45% in total spleen (8.23±0.68 mg vs. 4.55±1.26 mg, p=0.042, n=4). Although no change in the concentration of cholesterol in small intestine was observed (p=0.67), the triglyceride concentration of the treated group was 65% reduced (49.52±2.40 μg/mg vs. 17.09±4.8 μg/mg, p=0.042, n=4).

e. Summary

Limited treatment of lal−/− mice with LAL (10 injections in 30 days, 1.48 U/dose) led to gross, histologic and biochemical corrections of cholesterol and triglyceride levels in treated mice.

2. Plasma Chemistries and Lipid Levels in lal−/− and ldlr−/− Mice.

No differences in plasma glucose levels were observed in treated or untreated lal−/− or ldlr−/− mice although ldlr-l-mice have higher plasma glucose levels than wild type or lal−/− mice. The lal−/− and (ldlr−/− mice had increased plasma non-esterified fatty acids (NEFA) levels compared to the wild-type controls (162% and 227%, respectively). LAL administration was associated with increases of the NEFA by 32.6% in lal−/− mice and 24.5% in ldlr−/− mice. Plasma triglycerides levels decreased in treated lal−/− mice, but were unchanged in ldlr−/− mice. The HFCD produced hypercholesterolemia in ldlr−/− mice. The plasma free cholesterol concentration increased 22-fold and plasma cholesteryl ester concentration increased 13.8-fold compared to wild-type mice. The LAL treated ldlr−/− mice had decreases in plasma free cholesterol of 18.2% (p=0.0894) and in cholesteryl esters of 26.7% (P=0.0025). The free cholesterol and cholesterol ester levels were unchanged in treated lal−/− mice.

3. Histologic and Biochemical Effects of LAL Administration in ldlr−/− Mice.

a. Gross Anatomic and Histologic Studies

The visceral organs of these mice appeared normal. Whole mounts of the aortic arches were prepared from ldlr−/− mice and examined by transillumination. At 3.5 months, all (3/3) untreated ldlr−/− mice had extensive lesions of the arch and take-offs of the major vessels, i.e., brachiocephalic arteries. Although not quantitatively determined, LAL administration appeared to have little effect on these lesions in treated ldlr−/− mice.

To evaluate the coronary artery lesions, the hearts of treated and untreated ldlr−/− mice were sequentially sectioned and analyzed. Four ldlr−/− mice were untreated. One of these was found dead just before the LAL administration began (at age of 2.5 months). Eight mice received LAL and all survived for the entire study period. The results are summarized in Table 2. All untreated ldlr−/− mice had severe plaque lesions in aortic valve and ostia of the coronary arteries (see FIGS. 4A and B). Of the aortic valves examined in the treated group, two had mild to moderate (++), one had very mild (+), and two had no accumulation of foam cells (see FIG. 4C). The aortic valves from three treated mice were not examined histologically since they had been removed for the whole mount aortic arch studies.

The coronary lesions in the untreated group were extensive and multifocal. All had heavy infiltration of the coronary ostia by macrophages with plaques extending a considerable distance in the coronary arteries. Also, individual isolated and scattered plaques were found throughout the first third of the coronary arteries. In one case, the main branch of the left coronary was completely obliterated with an advanced lesion containing cholesterol crystals and apparent inflammatory. In comparison, ⅞ of the treated ldlr−/− mice had normal coronary vessels (see Table 2). One LAL treated ldlr−/− mouse had foamy cells in one small intramuscular coronary vessel. The other coronary arteries in this mouse were normal. This particular mouse (RA1) also had mild-moderate lesions of the aortic valve.

To obtain a more quantitative assessment of the coronary artery lesions in ldlr−/− mice, sequential H&E sections (total=210; 10 μm) of the heart were examined in an untreated mouse (RC2) and in one treated mouse (RB2). RC2 had multiple plaques in coronary arteries whereas RB2 had completely normal coronary arteries.

TABLE 2

Effect of LAL on the Aortic Valves and Coronary Arteries of ldlr-/- Mice

| Designation | Aortic Valve Lesion | Coronary Artery Lesions |
|---|---|---|
| LAL Untreated Mice | | |
| RC2 | ++++ | ++++ |
| RC3 | ++++ | +++ |
| RC4 | ++++ | ++++ |
| LAL Treated Mice | | |
| RA1 | ++ | + |
| RA2 | + | – |
| RA3 | + | – |
| RA4 | ++ | – |
| RB1 | – | – |
| RB2 | – | – |
| RB3 | ND | – |
| RB4 | ND | – |

++++ = severe lesions; +++ = moderate; ++ = mild-moderate; + = mild; – = no lesions; ND = Not done due to aortic arch removal for whole mounts.

These results show a major selective effect of a single fixed dose level of LAL on the presence of aortic valvular and coronary artery foam cell and progressive atherogenic lesions.

b. Biochemical Studies:

Plasma lipid results are reported above for the ldlr-/- treated and untreated groups. Liver and splenic cholesterol and triglyceride levels were increased over wild-type mice in the untreated ldlr-/- group. No significant effects were observed on the total cholesterol in liver (p=0.8816) and spleen (p=0.1061), or cholesterol concentration (0.0927) in the small intestine. The triglycerides were reduced 65.1% in total liver (91.54±1.98 mg vs. 59.60±6.86 mg; p=0.002), and 53.3% in total spleen (3.24±0.39 mg vs. 1.73±0.33 mg; p=0.0183). The concentration of triglycerides in small intestine also was reduced 43% (41.74±3.69 µg/mg vs. 23.79±2.08 µg/mg p=0.001).

c. Antibody Studies:

Serum was obtained at sacrifice from each mouse of each genotype and used in Western analyses. Prep #3 (2.65 ng/well) was used as antigen. Serum was used at 1:100 dilutions. All mice exposed to 10 injections of LAL gave positive western signals. The positive bands co-migrated with the LAL detected with rabbit anti-LAL. With one mouse serum positive signals were achieved with 1:100 to 1:6400 dilutions using Prep #3. Additional studies were conducted to determine the reactivity of these mouse sera to LAL or unglycosylated LAL produced in E.coli. Using 2.65 ng of antigen, the unglycosylated LAL gave very low to absent signals with all but one mouse serum. These results indicate that the antibody's specificity is directed more toward the oligosaccharides than the LAL protein in these conformations.

Summary of Data

The data from the ldlr-/- data show clear and dramatic effects of LAL administration on the presence of aortic valvular and coronary artery plaques and foam cells. All of the lesions were greatly diminished or absent in the treated mice compared to very severe lesions in the untreated cohort. The changes in hepatic, splenic and intestinal triglycerides indicate a direct effect of the LAL in these organs.

REFERENCES

1) Du, H.; Witte, D. F.; Grabowski, G. A. 1996, *Journal of Lipid Research*, vol. 37, pp. 937–949.
2) Hua, X., Yokoyama, C., Wu, J., Briggs, M. R., Brown, M. S., Goldstein, J. L., and Wang, X. 1993, *Proc. Natl. Acad. Sci.*, vol. 90, pp. 11603–11607.
3) Brown, M. S. and Goldstein, J. L. 1997, *Cell*, vol. 89, pp. 331–340.
4) Goldstein, J. L. and Brown, M. S. 1990, *Nature*, vol. 343, pp. 425–430.
5) Wang, X., Sato, R., Brown, M. S., Hua, X., and Goldstein, J. L. 1994, *Cell*, vol. 77, pp. 53–62.
6) Goldstein, J. L., Basu, S., and Brown, M. S. 1983, *Met. in. Enzymology*, vol. 8, pp. 241–260.
7) Goldstein, J. L., Dana, S. E., Faust, J. R., Beaudet, A. L., and Brown, M. S. 1975, *J. Biol. Chem*, vol. 250, pp. 8487–8495.
8) Kim, J. B. and Spiegelman, B. M. 1996, *Genes. Dev.* vol. 10, pp. 1096–1107.
9) Ericsson, J., Jackson, S. M., Lee, B. C., and Edwards, P. A. 1996, *Proc. Natl. Acad. Sci. USA* vol. 93, pp. 945–950.
10) Du, H., Witte, D. P., and Grabowski, G. A. 1996, *J. Lipid Res.* vol. 37, pp. 937–949.
11) Osborne, T. F. and Rosenfeld, J. M. 1998, *Curr. Opin. Lipidol.* vol. 9, pp. 137–140.
12) Sakai, J., Duncan, B. A., Rawson, R. B., Hua, X., Brown, M. S., and Goldstein, J. L. 1996, *Cell*, vol. 85, pp. 1037–1046.
13) Sakai, J., Nohturfft, A., Cheng, D., Ho, Y. K., Brown, M. S., and Goldstein, J. L. 1997, *J. Bio. Chem.*, vol. 272, pp. 20213–20221.
14) Yokoyama, C., Wang, X., Briggs, M. R., Admon, A., Wu, J., Hua, X., Goldstein, J. L., and Brown, M. S. 1993, *Cell*, vol. 75, pp. 187–197.
15) Hua, X., Wu, J., Goldstein, U., Brown, M. S., and Hobbs, H. H. 1995, *Genomics*, vol. 25, pp. 667–673.
16) Sato, R., Yang, J., Wang, X., Evans, M. J., Ho, Y. K., Goldstein, J. L., and Brown, M. S. 1994, *J. Biol. Chem.*, vol. 269, pp. 17267–17273.
17) Sakai, J., Nohturfft, A., Cheng, D., Ho, Y. K., Brown, M. S., and Goldstein, J. L. 1997, *J. Bio. Chem.* vol. 272, pp. 20213–20221.
18) Fielding, C. J. and Fielding, P. E. 1997, *J. Lipid. Res.* vol. 38, pp. 1503–1521.
19) Dietschy, J. M. 1990, *Hospital Practice*, pp. 67–78.
20) Rigotti, A., Trigatti, B. L., Penman, M., Rayburn, H., Herz, J., and Krieger, M. 1997, *Proc. Natl. Acad. Sci. USA*, vol. 94, pp. 12610–12615.
21) Temel, R. E., Trigatti, B., DeMattos, R. B., Azhar, S., Krieger, M., and Williams, D. L. 1997, *Proc. Natl. Acad. Sci. USA*, vol. 94, pp. 13600–13605.
22) Jian, B., Llera-Moyer, M., Ji, Y., Wang, N., Phillips, M. C., Swaney, J. B., Tall, A. R., and Rothblat, G. H. 1998, *J. Bio. Chem.*, vol. 273, pp. 5599–5606.
23) Johnson, M. S. C., Svensson, P. A., Helou, K., Billig, H., Levan, G., Carlsson, L. M. S., and Carlsson, B. 1998, *Endocrinology*, vol. 139, pp. 72–80.
24) Fluiter, K., Westhuijzen, D. R., and Berkel, T. J. C. 1998, *J. Bio. Chem.*, vol. 273, pp. 8434–8438.
25) Id. at 21.
26) Id. at 22.
27) Somerharju, P. and Lusa, S. 1998, *Biochem. Biophy. Acta.*, vol. 1389, pp. 112–122.
28) Assman, G. and Seedorf, U. 1995, *The Metabolic and Molecular Bases of Inherited Disease*, pp. 2563–2587.
29) Sheriff, S. and Du, H. 1995, *Am. J. Hum. Genet.*, vol. 57, page 1017A.
30) Sheriff, S., Du, H., Grabowski, G. A. 1995, *J. Biol. Chem.*, Vol. 270, pp. 27766–27772.
31) Amies, D., Merkel, M., Eckerskom, C., Greten, H. 1994, *Eur. J. Biochem.*, vol. 219, pp. 905–914.

32) Neufeld, E. F., Sando, G. N., Garvin, A. J., Rowl, W. 1977, *J. Supramol. Struct.*, vol. 6, pp. 95–101.
33) Sando, G. N., Henke, V. L. 1982, *J. Lipid Res.*, vol. 23, pp. 114–123.
34) Anderson, R. A., and Sando, G. N. 1991, *J. Biol. Chem.*, vol. 266, pp. 22479–22484.
35) Komaromy, M. C., Schotz, M. C. 1987, *Proc. Natl. Acad. Sci. USA*, vol. 84, pp. 1526–1530.
36) Lowe, M. E., Rosenblum, J. L. 1989, *J. Biol. Chem.*, vol. 264, pp. 20042–20048.
37) Shimida, Y., Sugihara, A., Tominaga, Y., Tsunaawu, S. 1989, *J. Biochem. (Tokyo)*, vol. 106, pp. 383–388.

What is claimed is:

1. A process for reducing atherosclerotic plaques in a mammal comprising administering to said mammal a safe and effective amount of lysosomal acid lipase, sufficient to effect a reduction in the amount of atherosclerotic plaques in said mammal.

2. The process of claim 1 wherein said lysosomal acid lipase targets a receptor site for uptake into lysosomes.

3. The process of claim 2 wherein said receptor site is selected from the group consisting of oligosaccharide recognition receptors and peptide sequence recognition receptors.

4. The process of claim 3 wherein said receptor site is a mannose receptor site.

5. The process of claim 1 wherein the lysosomal acid lipase has fewer than six N-linked acetylglycosylation residues.

6. The process of claim 5 wherein the N-acetylglycosylation residue is oligosaccharide-terminated.

7. The process of claim 6 wherein the oligosaccharide terminating residue is a mannose residue.

8. The process of claim 1 wherein the lysosomal acid lipase has more than six N-linked acetylglycosylation residues.

9. The process of claim 8 wherein the N-acetylglycosylation residue is oligosaccharide-terminated.

10. The process of claim 9 wherein the oligosaccharide terminating residue is a mannose residue.

11. The process of claim 1 wherein the lysosomal acid lipase is exogenously produced.

12. The process of claim 11 wherein said lysosomal acid lipase is in a pharmaceutically acceptable carrier and is administered either orally, parenterally, by injection, intravenous infusion, inhalation, controlled dosage release or by intraperitoneal administration.

13. The process of claim 12 wherein said lysosomal acid lipase is administered by intravenous infusion.

14. A method for treatment of atherosclerosis in a mammal comprising administering to said mammal a safe and effective amount of a lysosomal acid lipase, sufficient to treat said condition.

15. The method of claim 14 wherein said lysosomal acid lipase targets a receptor site for uptake into lysosomes.

16. The method of claim 15 wherein said receptor site is selected from the group consisting of oligosaccharide recognition receptors and peptide sequence recognition receptors.

17. The method of claim 16 wherein said receptor site is a mannose receptor site.

18. The method of claim 15 wherein the lysosomal acid lipase is exogenously produced.

19. The method of claim 18 wherein said lysosomal acid lipase is in a pharmaceutically acceptable carrier and is administered either orally, parenterally, by injection, intravenous infusion, inhalation, controlled dosage release or by intraperitoneal administration.

20. The method of claim 19 wherein the lysosomal acid lipase is administered by intravenous infusion.

21. The method of claim 14 wherein the lysosomal acid lipase has fewer than six N-linked acetylglycosylation residues.

22. The method of claim 21 wherein the N-acetylglycosylation residue is oligosaccharide-terminated.

23. The method of claim 22 wherein the oligosaccharide terminating residue is a mannose residue.

24. The method of claim 14 wherein the lysosomal acid lipase has more than six N-linked acetylglycosylation residues.

25. The method of claim 24 wherein the N-acetylglycosylation residue is oligosaccharide-terminated.

26. The method of claim 25 wherein the oligosaccharide terminating residue is a mannose residue.

27. A method for treatment of atherosclerosis in a mammal comprising administering to said mammal a safe and effective amount of exogenously produced lysosomal acid lipase sufficient to treat said condition.

28. The method of claim 27 wherein the lysosomal acid lipase is in a suitable pharmaceutically acceptable carrier.

29. The method of claim 28 wherein the lysosomal acid lipase is administered by intravenous infusion.

* * * * *